United States Patent [19]

Maggi

[11] Patent Number: 4,657,547
[45] Date of Patent: Apr. 14, 1987

[54] INTRAOCULAR LENS

[75] Inventor: Carlo Maggi, Rome, Italy

[73] Assignee: Surgivision Limited, St. Helier Jersey, Channel Islands

[21] Appl. No.: 852,371

[22] Filed: Apr. 16, 1986

Related U.S. Application Data

[63] Continuation of Ser. No. 386,943, Jun. 10, 1982, abandoned.

[30] Foreign Application Priority Data

Jun. 18, 1981 [IT] Italy ................ 35872/81[U]

[51] Int. Cl.⁴ .................................. A61F 2/16
[52] U.S. Cl. ........................................ 623/6
[58] Field of Search ............................... 623/6

[56] References Cited

U.S. PATENT DOCUMENTS

| | | | |
|---|---|---|---|
| 3,986,214 | 10/1976 | Krasnov | 623/6 |
| 4,158,030 | 6/1979 | Stoyan | 623/6 X |
| 4,244,060 | 1/1981 | Hoffer | 623/6 |
| 4,268,921 | 5/1981 | Kelman | 623/6 |
| 4,327,450 | 5/1982 | Girard | 623/6 |
| 4,361,913 | 12/1982 | Streck | 623/6 |

FOREIGN PATENT DOCUMENTS 810232  3/1959  United Kingdom ............ 623/6

OTHER PUBLICATIONS

"Pseudophakos" by N. S. Jaffe et al. (Book), the C. V. Mosby Company, St. Louis, 1978, pp. 39-40, FIGS. 4-5, on p. 39.

Primary Examiner—Ronald L. Frinks
Attorney, Agent, or Firm—Hopgood, Calimafde, Kalil, Blaustein & Judlowe

[57] ABSTRACT

An intraocular lens comprising a lens body provided with a supporting haptic part formed by at least two filiform elements fixed to the lens and appropriately oriented, each of said filiform elements presenting a length suitable to be laid in a surgically made, non-perforating incision located on the outer surface of the sclera wall of the eye so as to provide a firm anchorage which eliminates any tendency of the lens body to be displaced from the correct position in exact correspondence with the pupil of the eye.

11 Claims, 5 Drawing Figures

INTRAOCULAR LENS

This application is a Continuation of application Ser. No. 386,943 filed June 10, 1982, now abandoned.

This invention relates to a lens for the surgical correction of aphakic, which occurs after removal of the crystalline lens from the eye, or refractive defects such as myopia, hypermetropia, or astigmatism.

The eyeball is a nearly spherical globe with outer walls of a fibrous, firm, elastic consistency, which are for the most part opaque, with the exception of the area in front of the iris, which is transparent. The non-transparent part is called the sclera, while the transparent portion is the cornea.

Inside the eye, the space between the iris and the cornea is termed the anterior chamber and is filled with a transparent aqueous liquid, the aqueous humour, whereas the remaining part is almost entirely filled with a transparent gel termed the vitreous body.

Behind the iris and in front of the vitreous body there is the posterior chamber consisting of the crystalline lens and the circular ciliary body which supports it and also is filled with aqueous humour.

After removal of the crystalline lens (such as in cataract operation) a high degree of hypermetropia occurs, which was formerly corrected by the use of spectacles or contact lenses. The best possible vision is obtained however through the use of an intraocular lens surgically implanted, in either the anterior or posterior chamber. In the case of high myopia or other defects of refraction, the implant must be inserted into the anterior chamber, in front of the still present crystalline lens.

All intraocular lenses, of which at the current state of opthalmic technology there are many different versions, have a minimum diameter of 5-6 mm, whereas the previously mentioned anterior and posterior chambers of the eyeball have an internal diameter of approximately 10-11 mm, and 12-13 mm, respectively.

Consequently, in order for the lens to be placed in correspondence with the pupil, i.e. the circular aperture situated in the center of the iris, it is necessary for it to have a supporting haptic portion. In the various designs presently on the market the supporting haptic portion has a variety of shapes, all more or less functional, generally however they include two or three flexible filiform loops attached at one extremity to the lens and extending outwardly in a predetermined direction.

In prior art designs, in order to support the body of the lens in the proper position, the haptic portion is wedged between at least two opposite sides of the anterior or posterior chamber. When the lens is placed in the anterior chamber, the haptic portion rests in the angle between the anterior surface of the iris and the cornea. When positioned in the posterior chamber the haptic portion rests in the angle between the posterior surface of the iris and the ciliary body, or, if it has a suitable shape, sits astride the pupillary aperture where it is lodged like a collar-stud, the haptic portion being responsible for vertical equilibrium.

Previous types of intraocular lens have a total diametric length, including the optic and the haptic portions, not exceeding a total of 11-13 mm, i.e. the internal diameter of the anterior and posterior chambers respectively.

A disadvantage of these previous lenses is the difficulty of maintaining a stable position of the body of the lens in exact correspondence with the pupil. This instability is due to the tendency of the supporting ocular tissues to undergo a process of atrophy caused by the compression of the ocular tissues at the points of contact with the haptic portion of the lens. Attempts have been made to overcome the problem of atrophy by utilizing various types of lenses which are designed to be sutured to the iris, however, these attempts have not met with complete success due to the inconsistency and mobility of the iris.

The object of the present invention therefore is to provide an intraocular lens having an improved supporting haptic portion which provides stable and permanent positioning of the optic portion of the lens in correspondence with the pupillary aperture for an indefinite period of time. A further object of the present invention is to provide the above stable and permanent positioning without causing atrophy of the semi-rigid tissue of the sclera wall to which it is anchored, by extending the surface of contact between the tissues of the eye and the haptic portion of the lens, thereby minimizing the friction between the implant and the eye tissue.

The intraocular lens according to the present invention is characterized by the fact that the shape and length of the filiform element, which make up the supporting haptic portion, is suitable for being held and anchored in a surgically made non-penetrating incision in the exterior side of the sclera. Thus the minimum length of about 19 mm of the present implant far exceeds the maximum length of any prior implant of the type which is fitted like a spring into the anterior or posterior chamber. In fact, the supporting haptic portions of the intraocular lens according to the present invention have a length at least 7 mm each, and are buried in the sclera wall through a suitable superficial incision made in the sclera. Approximately 4.5 mm of the haptic portion of the lens is embedded in the sclera before it perforates the sclera wall at the base of the iris, and enters the anterior chamber at the lens near the pupil aperture.

Thus, the intraocular lens of the present invention comprises a prosthesis with very different characteristics from those already existing, whose shape is dependent on the anatomical features of the human eye. Even the surgical technique required to insert this new lens is completely different.

The objects and features of the present invention will be more fully understood from the following description taken in conjunction with the accompanying drawings in which.

With reference to the drawings, a lens body, for the surgical correction of aphakic by means of implantation in an eye which has undergone the removal of the crystalline lens is shown. In FIGS. 1 to 4 the dotted circle represents the average circumference of the posterior chamber of the eye, which has a diameter of 12-13 mm.

Figure 1:
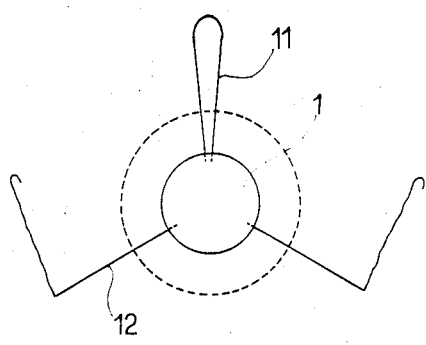
FIG. 1 is a plan view of one embodiment of the intraocular lens of the present invention.

Specifically, FIG. 1 depicts one embodiment of the intraocular lens of the present invention. The lens body, represented by reference number 1 is provided with haptic parts 11, 12 which are fixed at regular intervals of about 120°. The haptic parts are formed of threads, preferably having a section of 0.1 mm, which can take the form of loops or free threads. In the case of free threads these may have a total length of 5-6 cm, so that the surgeon may lay a suitable length in an incision made in the sclera, using the remaining portion of the thread as an anchoring suture in the sclera. The threads may be of plastic, metal or any other suitable material of appropriate thickness and elasticity, and can also conveniently terminate in either atraumatic needles or a small final loop.

Figure 3:
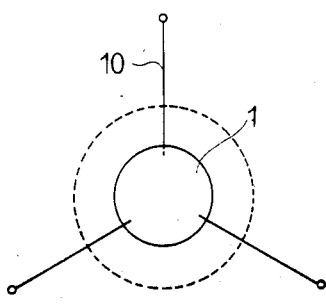
FIG. 3 is a plan view of a further embodiment of the intraocular lens of the present invention.

When the threads are made of plastic material, such as polypropylene, and are cut during surgery to the chosen length, their ends can be enlarged by heating (for example by cautery) so as to improve anchorage in the tissue. A frontal view of this kind of anchorage is shown in FIG. 3.

The threads constituting the haptic parts must be made of a material which is both inert and stable with regard to the ocular tissues, as is necessary in any surgical procedure. Additionally, the choice between the use of loops or free threads depends on the needs of the individual patient, the fact remaining that in either case the haptic parts are implanted in the sclera wall.

The present invention has a further advantage in that the shape of the intraocular lens may be varied. This variation was not possible with prior art intraocular lenses which were limited by the inner anatomical characteristics of the eye. Therefore, the total lengths of implants used up to the present time always slightly exceeded the internal diameter of the anterior or the posterior chamber where they are fitted in a spring-like manner. Thus it can be seen from FIGS. 1 to 4 that while the haptic parts of previously used intraocular lenses extend, at most, up to the dotted circumference, the loops and threads of the intraocular lens of the present invention extend beyond the dotted circumference, and are embedded in the strong sclera tissues so as to support, hold, and maintain the intraocular lens in its proper position.

Figure 2:
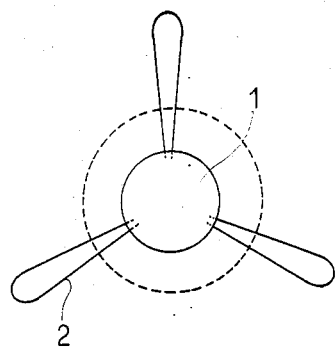
FIG. 2 is a plan view of a second embodiment of the intraocular lens of the present invention.

In FIG. 2 an intraocular lens is shown which is provided with three loops 2 disposed at 120° intervals and fixed to the lens body 1.

In the embodiment shown in FIG. 3, the haptic parts are formed of three threads 10, each of which is fixed to lens 1 and provided with an enlarged portion at its free extremity which serves to anchor it in the sclera wall. This enlargement can be produced at the moment of application by means of heating the extremity of the thread after it has been cut to the desired length by the operator for that individual patient. Alternatively, in order to anchor the threads to the tissues of the sclera wall, each of said threads may be terminated by an atraumatic needle or with a small loop.

Figure 4:
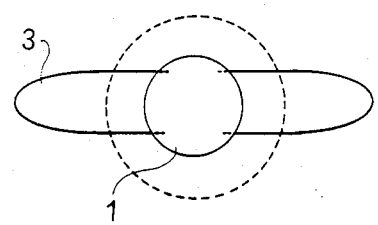
FIG. 4 represents a further variation of the intraocular lens of the present invention.
Figure 5:
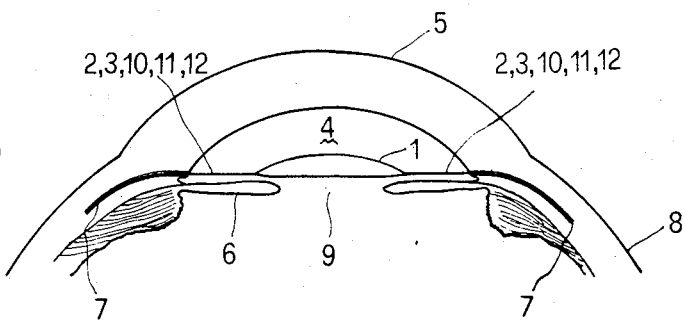
FIG. 5 is a diagrammatical view of the intraocular lens implanted in an aphakic eye.

A further embodiment of the present invention is shown in FIG. 4 in which the haptic part is formed by two loops 3 disposed 180° from each other.

Although in their essential conformation the loops depicted in FIGS. 1, 2 and 4 do not differ from conventional ones, their peculiarity with respect to the latter consists in their increased length which allows the use of a unique method of surgical application of the intraocular lens of the present invention in comparison with that of similar known lenses.

In view of the previous methods of implantation, the total length of the haptic part of the intraocular lenses produced to date, do not exceed the maximum inner diameter of the anterior or posterior chamber. In contrast, in the surgical application of the intraocular lens of the present invention in an aphakic eye (i.e. without the crystalline lens) the length of each loop or thread, is extended through the aqueous humour for the entire width of the anterior chamber 4 of the eye. The lengthening of each loop, or thread in the apparatus of the present invention enables portions of the haptic part to be placed in a respective incision 7 made in the sclera wall 8, which is the only non-soft tissue of the eye, thereby permitting a firm anchoring of the loops or threads, and eliminating any tendency for the lens body 1 to be displaced from its correct position in exact correspondence with pupil 9.

Although the surgeon may extend the haptic parts of the lens as far as desired posteriorly to the said dotted circumference, a minimum of 3-3.5 mm is preferred. In this way the total length of the implant will be at least 19 mm, as compared with the 13 mm of the largest implant previously available.

Although the present invention has been described in conjunction with the preferred embodiments, it is to be understood that modifications and variations may be resorted to without departing from the spirit and scope of the invention as those skilled in the art will readily understand. Such modifications and variations are considered to be within the purview and scope of the invention and the appended claims.

I claim:

1. An intraocular lens comprising a lens body and a supporting haptic part whereby the lens body is adapted to be positioned in the anterior chamber of the eye, said lens having a total length greater than 19 mm, said haptic part including at least three flexible filiform elements fixably attached to the edge of said lens body, each of said filiform elements extending from said lens body a length of at least 7 mm and adapted to allow at least one length of said filiform elements to be embedded in a surgically made non-perforating incision located on the outer surface of the sclera wall.

2. An intraocular lens according to claim 1, wherein said filiform elements are substantially straight and are symmetrically spaced around the periphery of the lens body.

3. An intraocular lens according to claim 2, wherein said filiform elements are at least five centimeters long.

4. An intraocular lens according to claim 1, wherein said filiform elements are in the form of loops symetrically spaced around the periphery of the lens body.

5. An intraocular lens according to claim 1, wherein each of said filiform elements is provided at its free extremity with an anchorage means adapted for anchoring said elements to the tissue of the sclera in which it is embedded.

6. An intraocular lens according to claim 5, wherein said anchorage means is an enlargement of the free extremity.

7. An intraocular lens according to claim 5, wherein said anchorage means is a loop formed at the free extremity.

8. An intraocular lens according to claim 5, wherein each of said filiform elements is provided with an atraumatic needle at its free extremity.

9. An intraocular lens according to claim 1, wherein said supporting haptic part is formed of one filiform element in the form of a loop and two substantially straight threads, disposed at 120° intervals around the periphery of the lens body.

10. An intraocular lens according to calim 2, wherein said supporting haptic part is formed of three substantially straight filiform elements disposed at 120° intervals around the periphery of the lens body.

11. An intraocular lens according to claim 4, wherein said supporting haptic part is formed of three filiform elements in the form of loops disposed at 120° intervals around the periphery of the lens body.

* * * * *